(12) United States Patent
Kaliszczak et al.

(10) Patent No.: US 11,964,280 B2
(45) Date of Patent: Apr. 23, 2024

(54) MICROFLUIDIC DEVICE FOR OBTAINING A PLASMA-REACTIVE MIXTURE AND METHOD OF IMPLEMENTATION

(71) Applicant: BELMONT DIAGNOSTICS, Éguilles (FR)

(72) Inventors: Maciej Kaliszczak, Belmont, MA (US);
Aymeric Vigneras, Belmont, MA (US);
Erwan Vigneras, Quimper (FR)

(73) Assignee: BELMONT DIAGNOSTICS, Éguilles (FR)

(*) Notice: Subject to any disclaimer, the term of this patent is extended or adjusted under 35 U.S.C. 154(b) by 0 days.

(21) Appl. No.: 18/260,542

(22) PCT Filed: Jan. 12, 2023

(86) PCT No.: PCT/EP2023/050672
§ 371 (c)(1),
(2) Date: Jul. 6, 2023

(87) PCT Pub. No.: WO2023/179927
PCT Pub. Date: Sep. 28, 2023

(65) Prior Publication Data
US 2024/0082840 A1 Mar. 14, 2024

(30) Foreign Application Priority Data
Mar. 25, 2022 (FR) .................... 2202677

(51) Int. Cl.
*B01L 3/00* (2006.01)
*A61B 5/151* (2006.01)

(52) U.S. Cl.
CPC ........ *B01L 3/502753* (2013.01); *A61B 5/151* (2013.01); *B01L 3/50273* (2013.01);
(Continued)

(58) Field of Classification Search
CPC . A61B 5/151; B01L 3/50273; B01L 2200/16; B01L 2300/0681;
(Continued)

(56) References Cited

U.S. PATENT DOCUMENTS

| | | |
|---|---|---|
| 2012/0275955 A1 | 11/2012 | Haghgooie et al. |
| 2014/0305823 A1 | 10/2014 | Gelfand et al. |

(Continued)

FOREIGN PATENT DOCUMENTS

WO    2014172247 A1    10/2014

OTHER PUBLICATIONS

International Search Report (PCT/ISA/210) and Written Opinion (PCT/ISA/237) with translation dated Feb. 10, 2023, by European Patent Office as the International Searching Authority for International Application No. PCT/EP2023/050672. (15 pages).

*Primary Examiner* — Matthew D Krcha
*Assistant Examiner* — Tingchen Shi
(74) *Attorney, Agent, or Firm* — BUCHANAN INGERSOLL & ROONEY PC

(57) ABSTRACT

A microfluidic device for obtaining a homogenous plasma-reagent mixture includes a collection module for blood plasma arranged to passively separate the blood plasma from a drop of blood taken, a capillary channel in fluidic connection with said collection module and a storage reservoir for a reagent in fluidic connection with said capillary channel. The device also contains a mixing chamber in fluidic connection with said capillary channel equipped with a flow outlet. The volume of said storage reservoir for reagent being greater than the sum of the volumes of said capillary channel and of said mixing chamber, setting the reagent in motion, after saturation of said capillary channel with blood plasma, induces a flow of the homogenous plasma-reagent mixture from the flow outlet.

8 Claims, 4 Drawing Sheets

(52) U.S. Cl.
CPC ... *B01L 2200/16* (2013.01); *B01L 2300/0681* (2013.01); *B01L 2300/0867* (2013.01); *B01L 2300/12* (2013.01); *B01L 2400/0406* (2013.01); *B01L 2400/0457* (2013.01)

(58) Field of Classification Search
CPC ......... B01L 2300/0867; B01L 2300/12; B01L 2400/0406; B01L 2400/0457; B01L 3/502753
See application file for complete search history.

(56) References Cited

U.S. PATENT DOCUMENTS

| | | |
|---|---|---|
| 2014/0309557 A1 | 10/2014 | Fletcher et al. |
| 2017/0001192 A1 | 1/2017 | Kelly et al. |
| 2017/0343533 A1* | 11/2017 | Liu .................... B01D 63/088 |
| 2019/0111421 A1 | 4/2019 | Johnson |

* cited by examiner

MICROFLUIDIC DEVICE FOR OBTAINING A PLASMA-REACTIVE MIXTURE AND METHOD OF IMPLEMENTATION

The present invention concerns, in general terms, the field of blood test devices. The invention relates more particularly to a microfluidic device for obtaining a plasma-reagent mixture and a method of implementing such a device so as to make it possible, ultimately, to quantify a blood biomarker of interest.

According to the World Health Organization, in 2019, seven out of ten principal causes of death worldwide were chronic diseases and the percentage of deaths associated with such diseases is steadily increasing. Chronic diseases are defined as developing diseases that have lasted for several months. Many studies have shown that early detection of such diseases increases patient survival chances. For example, in the case of several types of cancer, survival can be more than three times greater when the cancer is diagnosed early (stage one or two). Similarly, early detection of markers associated with acute diseases or symptoms as well as pathogenic agents, such as for example, the Covid 19 virus, the pathogenic element associated with Lyme disease or that associated with septicaemia or even the human immunodeficiency virus (known by the abbreviation HIV), makes it possible to assess for high pathological risk and rapidly direct care, which may need to be immediate and vital in some cases, in order to promote recovery.

For this reason, blood biomarkers, which are biological characteristics, are arousing increasing interest as an indicator of a normal or a pathological biological process. In this respect, each biomarker has specific characteristics that allow it to provide items of information associated with an underlying pathophysiological process and/or data on the progression of a disease. By analogy, biomarkers are to medical practitioners what fingerprints are to the police: genuine signatures that make it possible to identify not an individual, but a disease. Biomarkers consist of molecules (proteins, hormones, etc.) and cells, the presence or abnormal concentration of which in the blood, more particularly in the blood plasma, is evidence of the existence of a pathology. Blood plasma is the liquid component of blood without the red blood cells, the white blood cells, the platelets and other contaminants, constituting approximately fifty-five percent of the total blood volume and estimated to contain at least three hundred proteins.

A biomarker can be present in patients suffering from a specific disease and absent in individuals in good health or affected by other diseases. However, accurate quantification of a biomarker makes it possible to mirror the development of a pathology. For example, the quantity of a biomarker can increase or reduce according to whether the disease deteriorates or improves, and vice versa. Thus, such quantitative indicators make it possible:

- to refine a prognosis by delivering complete information in order to characterize a disease (or the presence of a pathogenic agent) in an individual and thereby optimize their care;
- to adapt the most suitable treatment to a patient. In this respect, some people assimilate a medicament particularly rapidly, according to their metabolism. In this case, the medicament can pass more rapidly into the blood, its effects are increased, and it is therefore necessary to reduce the dosage usually prescribed;
- to monitor the effects of a therapy. For example, in the case of cancer, the cancer cells release various molecules into the bloodstream. If the concentration thereof increases over time, this may mean that the cancer has recurred. Quantification of the blood biomarkers therefore appears to be an indispensable tool for personalized medicine.

Traditionally, such a quantification is possible by recourse to the traditional tried and tested blood sample process. However, such a process needs a significant quantity of blood, the intervention of trained personnel and the use of specialized equipment, which results in a costly and time-consuming technique. In fact, this requires having a prescription from a doctor to request a blood sample, making an appointment with a nurse or laboratory, assuming matching availability of the health care personnel and the patient, waiting for the blood tests to be carried out at the laboratory and transfer of the results to the doctor, followed by interpretation thereof.

In order to overcome part of the aforementioned time-consuming steps, self-administered blood sample kits are also known in the market, which can be carried out at home by any individual, using a smaller volume of blood, as disclosed by patent applications US 2019/0111421, US 2014/0309557 or WO 2014/172247A1 proposing devices for the collection and storage or transfer of a bodily fluid, in this case blood. However, as in the case of a blood sample, such devices need the services of a laboratory to carry out the tests with specialized equipment and analysis of the results by trained personnel.

Patent application US 2017/0001192 tries to partially respond to these drawbacks by proposing a test device allowing evaluation of biomarkers in a bodily fluid without recourse to one or more external resources (laboratory, trained personnel, etc.). However, such a device makes it possible to reach a qualitative result of a biomarker (presence or absence of the biomarker) but not a quantitative result for every biomarker. Such a solution thus requires a laboratory analysis in order to quantify the biomarker of interest and does not make it possible to identify proteins present in low quantity (of the order of one microgram-nanogram/millilitre and below) that may be the essential markers.

The documents US 2014/0309557 and WO 2014/172247A1 describe a device for sampling, storage and transfer of a blood sample. Such a device contains, prior to said blood sample, an anticoagulant additive to ensure the transport of said blood sample to a laboratory responsible for carrying out a test with respect to plasma taken from said blood sample. However, like a traditional blood sample process, separating the plasma from the other blood constituents needs the use of specific laboratory equipment, in this case in particular a centrifuge, and trained personnel.

Only a quantitative result of biomarkers, as previously indicated, allows enhanced monitoring of the health of a patient. Thus, the present invention aims to overcome the aforementioned drawbacks, in particular to propose a microfluidic device for obtaining a homogenous plasma-reagent mixture and the simplified implementation method thereof so as to have, ultimately, a direct and rapid quantification of a blood biomarker, at home, that can be used based on a single drop of blood and capable of being implemented by any user, while ensuring reliability and reproducibility of the results due to accurate volumetric analysis/volume control, at all the steps of the process, of the blood plasma and of the reagent used.

In this respect, a first subject of the invention relates to a microfluidic device for obtaining a homogenous plasma-reagent mixture comprising:

- a blood collection module;

a first capillary channel having a first end in fluidic connection with said collection module;

a storage reservoir for a fluid in fluidic connection with said first capillary channel;

a mixing chamber in fluidic connection with a second end of the first capillary channel arranged to passively induce a homogenous mixture of fluids originating from said first capillary and having a flow outlet for said homogenous mixture;

a means for preventing any fluidic return to the collection module.

In order to conduct a test at home or on the move and thus obviate the need to use third-party equipment and to carry out a laboratory test by trained personnel, such a microfluidic device for obtaining a homogenous plasma-reagent mixture is arranged such that the plasma collection module contains:

a semi-permeable membrane arranged to receive a quantity of blood and designed to separate the blood constituents, by gravity when said semi-permeable membrane is substantially horizontal, according to the sizes thereof and thus to trap said constituents other than the blood plasma;

a specific surface arranged between said semi-permeable membrane and the first end of the first capillary channel and having hydrophobic, hydrophilic and surface tension properties in order to extract the blood plasma from the semi-permeable membrane and cause said blood plasma to flow in said first capillary channel.

Moreover, such a microfluidic device for obtaining a homogenous plasma-reagent mixture is arranged such that:

the first capillary channel has determined dimensions between the fluidic connection of said storage reservoir with the first capillary channel and said second end of said first capillary channel, in order to control the quantity of blood plasma when the first capillary channel is saturated with blood plasma;

the fluid contained in the storage reservoir is a reagent intended to be mixed with the blood plasma;

said storage reservoir is arranged to:

contain a volume of reagent greater than the sum of the fluid volumes that the first capillary channel and the mixing chamber can contain;

have an actuator designed to induce a forced flow of said reagent in the first capillary channel driving a flow of a homogenous plasma-reagent mixture through said flow outlet of the mixing chamber when said actuator is controlled after saturation of the first capillary channel with blood plasma.

So as to optimize the capillarity phenomenon and to maximize setting the blood plasma in motion from the semi-permeable membrane to the first capillary channel, the first end of said first capillary channel can be positioned substantially at the centre of said collection module.

In order to concentrate the blood deposited on the semi-permeable membrane and any propagation of the blood outside the surface thereof, the collection module of such a device can contain a membrane holder arranged to concentrate the blood on said semi-permeable membrane.

Advantageously, the specific surface can be constituted by polymethyl methacrylate, a thermoplastic polymer, polyacrylamide, polyurethane, poly(hydroxyethyl methacrylamide) or polyethylene glycol derivatives.

In order to optimize a passive and homogenous mixture of the blood plasma and of the reagent flowing in said first capillary channel, said mixing chamber can contain a network of channels respectively arranged in zigzags, coils, or chevrons, to passively induce said homogenous plasma-reagent mixture.

A second subject of the invention consists of a method for the implementation of a microfluidic device for obtaining a homogenous plasma-reagent mixture according to the invention. Such a method contains the following steps:

a step of depositing blood on the semi-permeable membrane of the plasma collection module, when said device is positioned such that the semi-permeable membrane is horizontal;

a step of saturating the first capillary channel with blood plasma;

a step, after said step of saturating the first capillary channel with blood plasma, of controlling the actuator of the storage reservoir inducing the forced flow of a reagent, contained beforehand in said storage reservoir, into the first capillary channel following saturation of the mixing chamber;

a step of collecting a homogenous plasma-reagent mixture from the flow outlet thereof.

By way of example of an advantageous implementation, the step of saturation of the first capillary channel with blood plasma can consist of waiting, as soon as the blood plasma flows in the first capillary channel, for a predetermined duration, as a function of the dimensioning of the first capillary channel.

In order to produce an analysis of said plasma-reagent mixture, the step of collecting the homogenous plasma-reagent mixture can consist of positioning a reactive strip downstream of the flow outlet of the mixing chamber such that said strip collects all or part of said homogenous plasma-reagent mixture.

The disclosure of the invention will now be continued via the detailed description of an embodiment, given hereinafter by way of non-limitative illustration, with reference to the attached drawings, in which.

As an introduction, it is important to recall the definition of the following terms:

hydrophilia is a term used to characterize a molecular property resulting from the existence of strong attractions or affinities between certain molecular groups and water. In other words, it is the affinity of a substance for water or the capability of being wetted by water without being dissolved;

hydrophobia is a term used to denote and characterize the surfaces that seem to "repel water", or that water seems to have difficulty wetting, in particular due to the fact that the water molecules are polar and have a preferential attraction for the other polar molecules;

surface tension/surface energy and contact angle: an energy per unit of surface area, the origin of which is the cohesion force between identical molecules, is associated with an interface that separates two different media. A representative example of such a quantity is that of a drop of liquid deposited on a support/solid: such a drop forming an angle, called contact angle, which varies as a function of the surface tension of the support/solid. Thus, if there is repulsion between the liquid and the solid, the drop placed on the solid will tend to "regroup" and to adopt a spherical shape, thus having a "high" contact angle. Conversely, if there is attraction between the liquid and the solid, the drop placed on the solid will tend to extend, thus having a "low" contact angle. In the case of a liquid such as water, if the angle of contact is greater than zero degrees and less than ninety degrees, water tends to extend and wet the support/solid: this is then known as a wetting or hydrophilic surface. In the event that the contact angle is substantially equal to zero degrees, wetting is total. Thus, the higher the contact angle, the less the support/solid is wettable by water;

capillarity is a property of fluids dependent on the surface tension of such fluids, giving them the capacity to rise or fall through a capillary tube/channel. The thinner said tube, the greater the distance travelled by a liquid in the tube, the blood plasma is the liquid portion of the blood, composed at over ninety percent of water. Thus, blood plasma is considered mainly hydrophilic.

Figure 1:
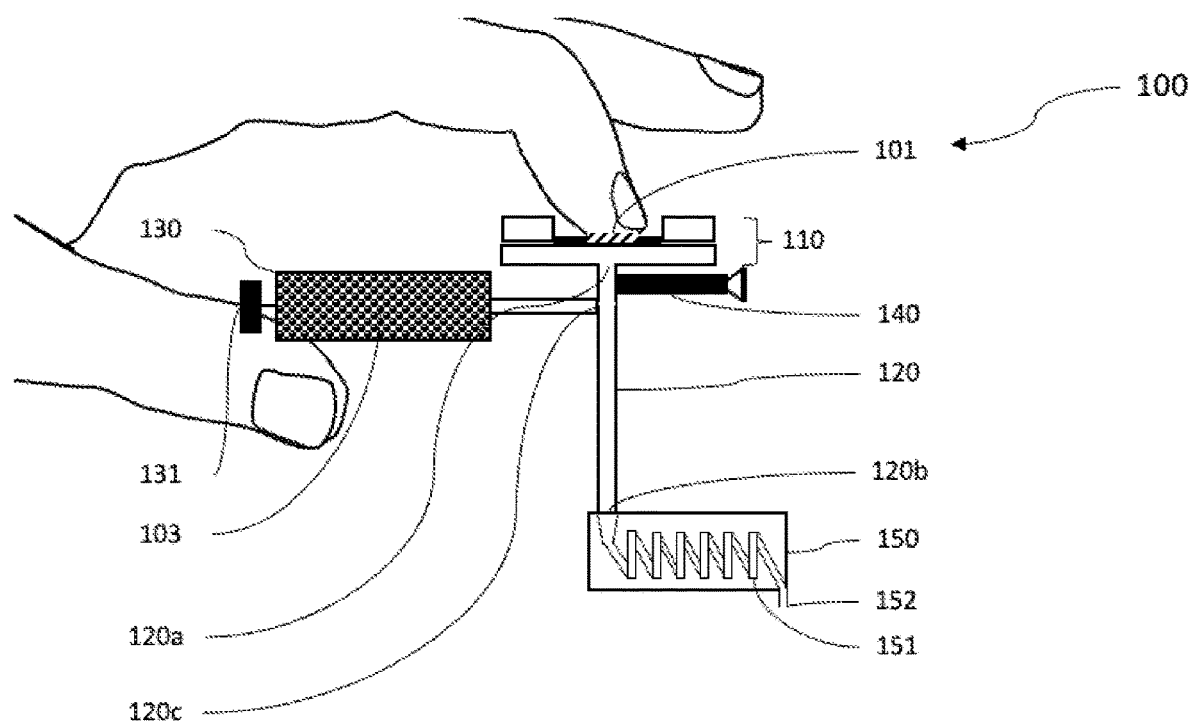
FIG. 1 shows a preferred example of implementation of a microfluidic device for obtaining a plasma-reagent mixture according to the invention.

A preferred example of the microfluidic device 100 for obtaining a homogenous plasma-reagent mixture according to the invention is shown in FIG. 1. Said device 100 is composed of at least one blood plasma collection module 110 in fluidic connection with a first end 120a of a capillary channel 120, itself in fluidic connection with a storage reservoir 130 for a reagent 103. Within the meaning of the invention, by "reagent" is meant any fluid making it possible to render certain physicochemical parameters of blood plasma, such as the pH for example, optimal for the conformation of a protein subject to quantification. Such a reagent can moreover be chosen to control the speed of fluidic flow in the device and to limit any non-specific interaction of the proteins of interest (biomarkers) with the semi-permeable membrane and the internal walls of the device. By way of non-limitative examples, it can be composed of proteins such as BSA (bovine serum albumin), detergent (such as Tween 20), a saline solution (such as phosphate buffer saline) and/or an antibacterial solution, (such as sodium azide). Such a reagent is distinguished from stabilizers or anticoagulants that are found in certain devices for sampling and transporting blood such as those described for example in the aforementioned documents US 2014/0309557 and WO 2014/172247A1, the only function of which is to allow the storage of blood samples until reaching an analysis centre and which do not need to be set in motion within said transport devices. Said device 100 comprises, moreover, a means 140 for preventing any fluidic return to said collection module 110, positioned upstream of the fluidic connection of said storage reservoir 130 with said capillary channel 120. The device 100 also includes a mixing chamber 150 in fluidic connection with a second end 120b of the capillary channel 120. Said device 100 is implemented by said method 200, shown on the flow chart in FIG. 2, so as to obtain a homogenous plasma-reagent mixture 104 based on a minimum quantity of blood 101, more particularly blood plasma, of the order of ten to one hundred microlitres, such a mixture 104 making it possible, ultimately, to quantify a blood biomarker of interest by using a test strip directly on site, i.e., for example, at home by the person having taken the blood sample, generally the patient, or at the patient's bedside, in an ambulance, or in the doctor's consulting room.

Figure 3:
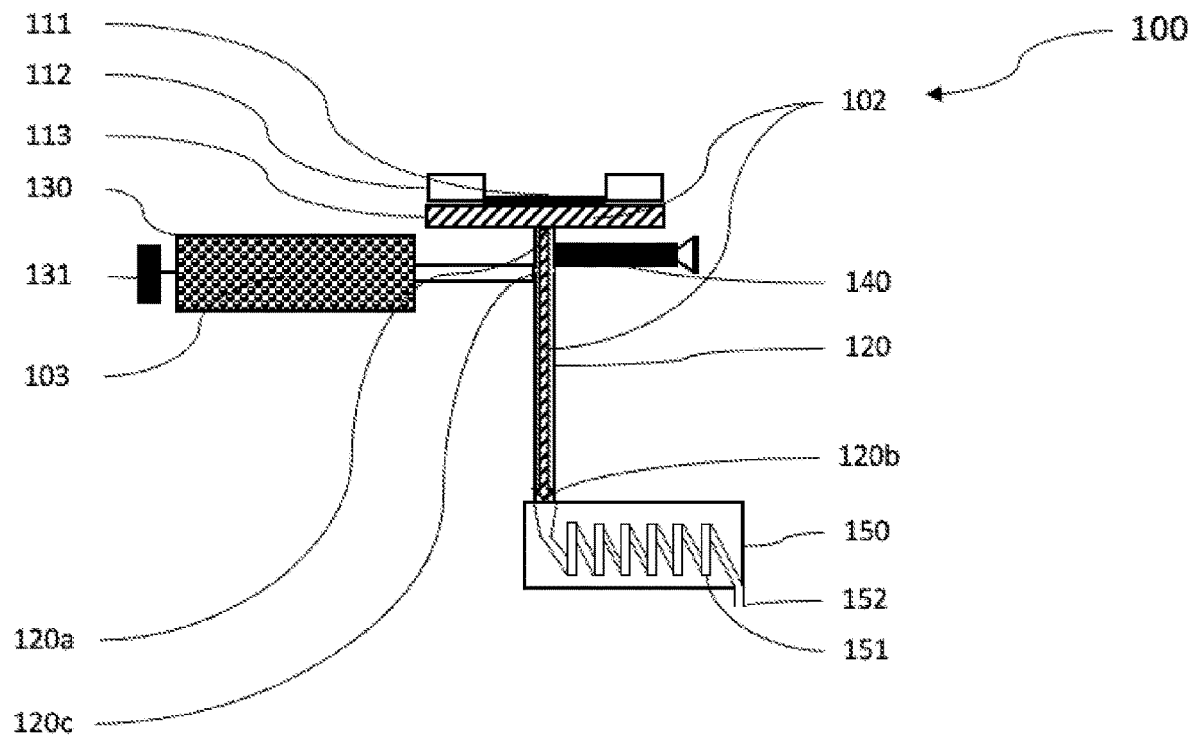
FIGS. 3 to 7 are diagrammatic views of the device according to the invention showing different steps for the implementation of said device according to the invention.

A step 210 of said method 200 consists of supplying with blood plasma 102 said collection module 110 that is in fluidic connection with the first end 120a of said capillary channel 120, considered as the upper portion of said capillary channel 120, the second end 120b being considered as the lower portion of said capillary channel 120 when said capillary channel 120 is oriented in space as indicated in FIG. 1. Such a supply of blood plasma 102 can entail depositing blood in the collection module 110, when said collection module 110 is arranged to passively separate said blood plasma 102 from said blood, or consist of directly depositing plasma in said collection module. Thus, as shown in FIG. 3, said blood plasma 102 can be displaced automatically in the capillary channel 120 by capillarity, the phenomenon defined above in the present description, and thus flow vertically (from top to bottom according to FIG. 1) along said channel 120. In a preferred but non-limitative embodiment, so as to optimize such a capillarity phenomenon and to maximize the associated effect, it is preferable for the first end 120a of the capillary channel 120 to be positioned substantially at the centre of the lower surface of the collection module 110. In a variant, said first end 120a of the capillary channel 120 can be positioned between the outer edge and the centre of the lower surface of the collection module 110.

As stated above, the blood plasma 102 can advantageously be isolated, using said device 100 according to the invention, based on one or more drops of blood 101 taken by the user themself. Such a drop 101 can be collected for example using a lancet device that the user can apply to the end of their finger, or any other suitable device. As soon as the end of the user's finger is pierced or pricked by the lancet, the user can thus displace their finger at the level of the blood plasma collection module 110 in order to deposit the drop of blood 101 there, as shown in FIG. 1. To this end, as shown in FIG. 3, in a preferred example, said module 110 contains a semi-permeable membrane 111 across which the collected blood 101 can pass or flow. Such a semi-permeable membrane 111, for example Pall's Vivid™ brand, known and available on the market, thus makes it possible to separate the blood constituents as a function of the sizes thereof. Said semi-permeable membrane 111 is thus arranged to receive a quantity of blood 101 and to separate the blood constituents, by gravity when said semi-permeable membrane 111 is substantially horizontal, according to the sizes thereof, such that the white blood cells, the red blood cells and other large-diameter constituents can be trapped in said membrane 111, unlike the blood plasma 102, which is capable of flowing through said membrane. A percentage filtering efficiency of the order of sixty percent or above is envisaged. Thus, when said membrane 111 is substantially horizontal, the blood plasma 102 can be collected below said membrane 111 by gravity.

Moreover, so as to concentrate the blood 101 on said membrane 111 and avoid the blood 101 propagating outside the separation/filtering surface, delimited by the edges of said membrane 111, the collection module 110 can contain a membrane holder 112 positioned so as to press and hold the edges of said membrane 111. However, a person skilled in the art would not be bound by such a membrane holder device 112 and would be able to envisage any type of device allowing said function to be fulfilled.

Once the blood plasma 102 has been able to be separated from the other blood constituents, it is necessary to be able to recover it to allow continuity of said plasma 102 in said device 100 to be established. In this respect, said blood plasma 102 must be removed from the semi-permeable membrane 111 and also conveyed to the capillary channel 120. The invention is clearly distinguished from the teaching drawn from the document US 2012/0275955A1 which imposes the presence of a vacuum chamber in order to create a flow and forcibly separate plasma from a blood sample through a membrane. Such a forced filtration is likely to deform the membrane, or even to generate a phenomenon known as haemolysis according to which red cells can fracture under the effect of said flow through the membrane, thus degrading the plasma obtained. In fact, the cell constituents released (e.g., potassium, lactate dehydrogenase, haemoglobin) during such a destruction can degrade the relevance and the accuracy of a subsequent quantification of proteins based on said haemolyzed plasma. Unlike such a technical teaching drawn from the document US 2012/0275955A1, as shown in FIG. 1, the collection module 110 according to the invention can contain a specific surface 113, positioned upstream of the fluidic connection of said plasma collection module 110 and of the first end 120a of the capillary channel 120. Such a specific surface 113 makes it possible, by gravity, to extract the plasma 102 from said semi-permeable membrane 111 and to make it flow and progress by capillarity within the device 100 to reach the capillary channel 120. The invention thus makes it possible to prevent any risk of haemolysis or of deformation of the semi-permeable membrane 111, preserving the blood plasma 102 thus isolated and consequently maintains the relevance of any quantification relating to said blood plasma 102.

In order to allow continuity of the blood plasma 102 to be established in the device 100 and not only the retention of said plasma 102, in other words to absorb the blood plasma 102 from said specific surface 113 and passively set it in motion in the capillary channel 120, the specific surface must have an optimized balance between hydrophobic and hydrophilic properties, properties specified above in the present description.

Indeed, due to the fact that the blood plasma 102 is mainly hydrophilic (around ninety percent of which is formed by water) but also contains hydrophobic matter, said specific surface 113 must have a suitable surface tension and be constituted by a hydrophilic material without being water-soluble. Said specific surface 113 is thus arranged between the semi-permeable membrane 111 and the first end 120a of the first capillary channel 120 and has determined hydrophobic, hydrophilic and surface tension properties in order to extract the blood plasma 102 from the semi-permeable membrane 111 and cause the flow of or set in motion said blood plasma 102 in said first capillary channel 120.

In this respect, said specific surface 113 can preferably be constituted by polymethyl methacrylate, a thermoplastic polymer known by the abbreviation PMMA, having a mainly hydrophilic character (the angle of contact with water is of the order of sixty-eight degrees) and exhibiting a good balance between the hydrophobic groups (methylene) and the hydrophilic groups (carbonyl). However, a person skilled in the art would not be bound by such a material and would be able to envisage any other type of material making it possible to obtain such properties or the equivalent, such as for example, polyacrylamide, polyurethane, poly(hydroxyethyl methacrylamide) or polyethylene glycol derivatives.

In a variant or in addition, it is possible to optimize or improve the hydrophilic characteristics of the chosen material(s) with recourse to treatments making it possible to functionalize the surfaces of said materials, in particular to modify the surface tension thereof, such as for example gas plasma treatments (argon, oxygen, etc.), corona treatments or even chemical treatments (with sodium hydroxide, polyvinyl alcohol or hydroxy propyl methyl cellulose, etc.).

Figure 2:
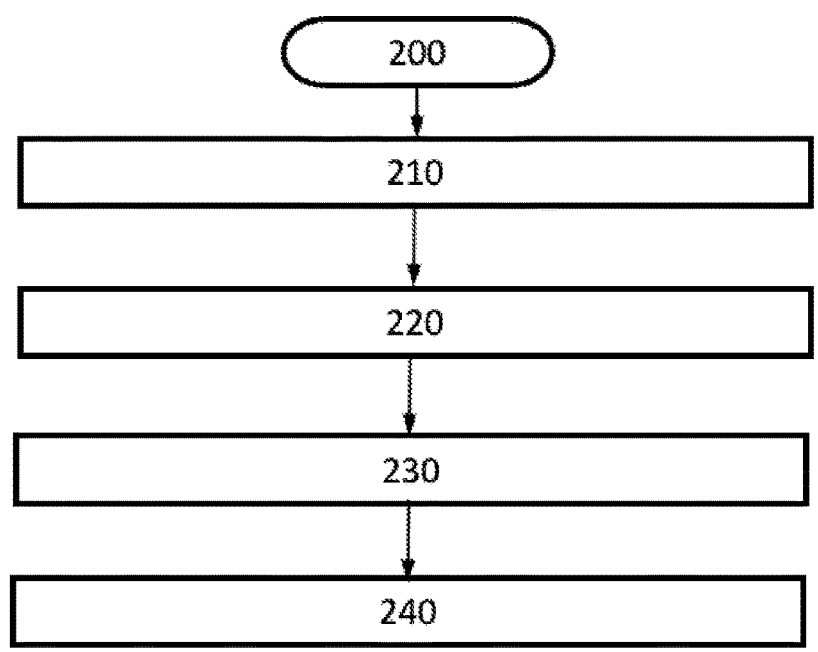
FIG. 2 shows a flow chart representing steps of the method for the implementation of a device according to the invention.
Figure 4:
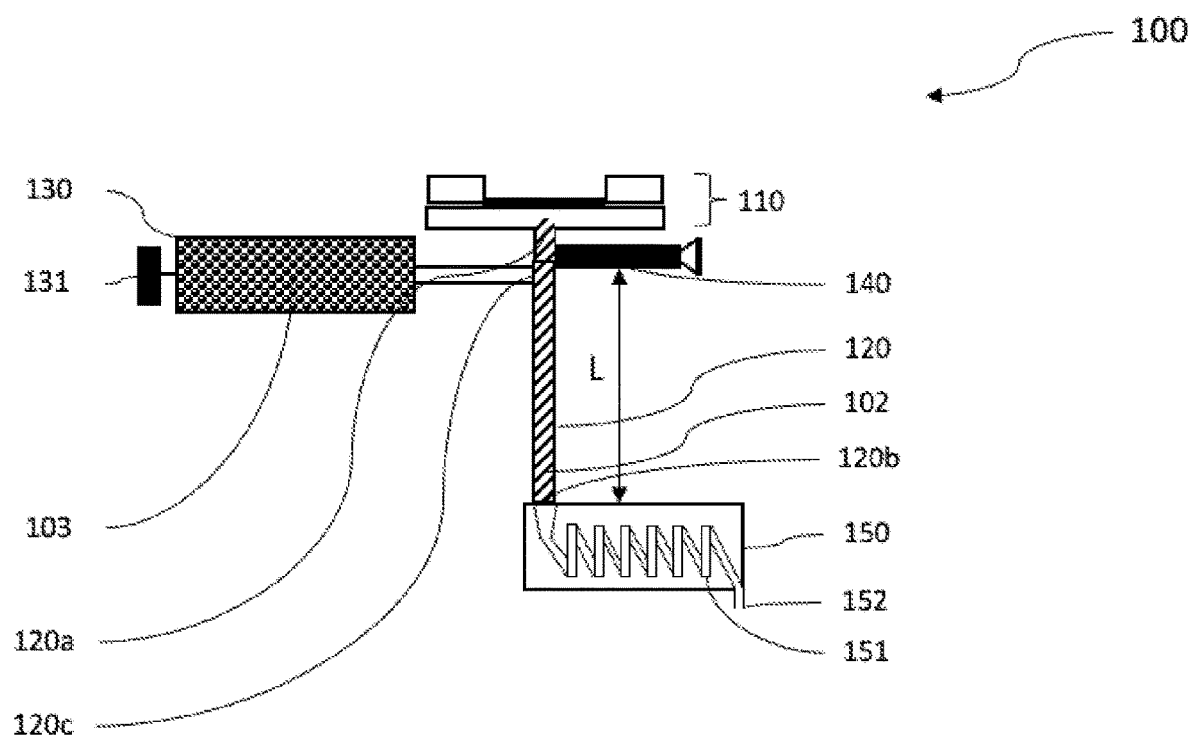

Once the step 210 is complete, said step consisting of depositing blood 101 or blood plasma 102 in the plasma collection module 110 in order to obtain established continuity or setting in motion of said blood plasma 102 in the capillary channel 120, as shown in FIG. 2, a method 200 contains a step 220 of saturating the capillary channel 120 with blood plasma 102. This step 220 thus makes it possible to have a constant controlled volume of blood plasma 102 within the capillary channel 120, the quantity of said blood plasma in the capillary channel 120 thus being perfectly adjusted. To this end, the capillary channel 120 has determined dimensions including a predefined length L, as shown in FIG. 4. Said length L corresponds to the defined length between the fluidic connection of said storage reservoir 130 with the capillary channel 120 and said second end of said capillary channel 120. Said length L thus makes it possible, for a given cross section diameter of said capillary channel 120, to determine and control a quantity of blood plasma 102 when the capillary channel 120 is saturated with plasma 102. By way of example, for blood plasma volumes of the order of ten to one hundred microlitres, the capillary channel 120 can have an internal diameter substantially comprised between zero point three and one point five millimetres and a length L comprised between fifteen and eighty millimetres. Such a capillary channel 120 can be made from glass, plastic or constituted by any other material having suitable characteristics (hydrophilic properties, properties promoting capillarity, electrostatic properties and even mechanical properties such as elasticity). However, preferably, the plastic materials are favoured because the functionalization of the surface thereof (making it possible in particular to increase the hydrophilic properties and/or improve the capillarity) is easier than for the other materials. Furthermore, such a capillary channel 120 can be integrated in said device 100 in the form of a complete element. However, in a variant, in the event that the device 100 contains a flexible or rigid body, not shown in the figures for reasons of simplicity, housing the constituents of said device 100, such as the collection module 110, the capillary channel 120, the storage reservoir 130, the mixing chamber 140, such constituents could be created directly by moulding or additive manufacturing of said body or by removal of material therefrom by using a laser or machining technology.

Moreover, so as to promote the saturation of the capillary channel 120 with blood plasma 102, the volume of the capillary channel 120 can be dimensioned to be less than the volume of the blood plasma 102 contained in the collection module 110. In a variant, the step 220 of saturation of the capillary channel 120 with blood plasma 102 can consist of waiting for a predetermined duration, defined according to the dimensioning of said capillary channel 120, as soon as the blood plasma 102 flows along the capillary channel 120. However, a person skilled in the art would not be bound to limiting the invention to such a step and would be able to envisage any other manner of implementing the saturation step 220, such as, for example, the appearance of a coloured indicator when the capillary channel 120 is saturated with blood plasma 102 or the use of an item of information delivered by a sensor, for example an optical sensor, positioned in immediate proximity to the second end 120b of said channel 120.

So as to avoid any reflux or overspill, according to a first mode, the means 140 for preventing any fluidic return to the collection module 110 can consist of a non-return valve. Thus, the latter permits the passage of said blood plasma 102 into the capillary channel 120 from the collection module 110 and prevents any return flow of said plasma 102 from the capillary channel 120 to the collection module 110.

Figure 5:
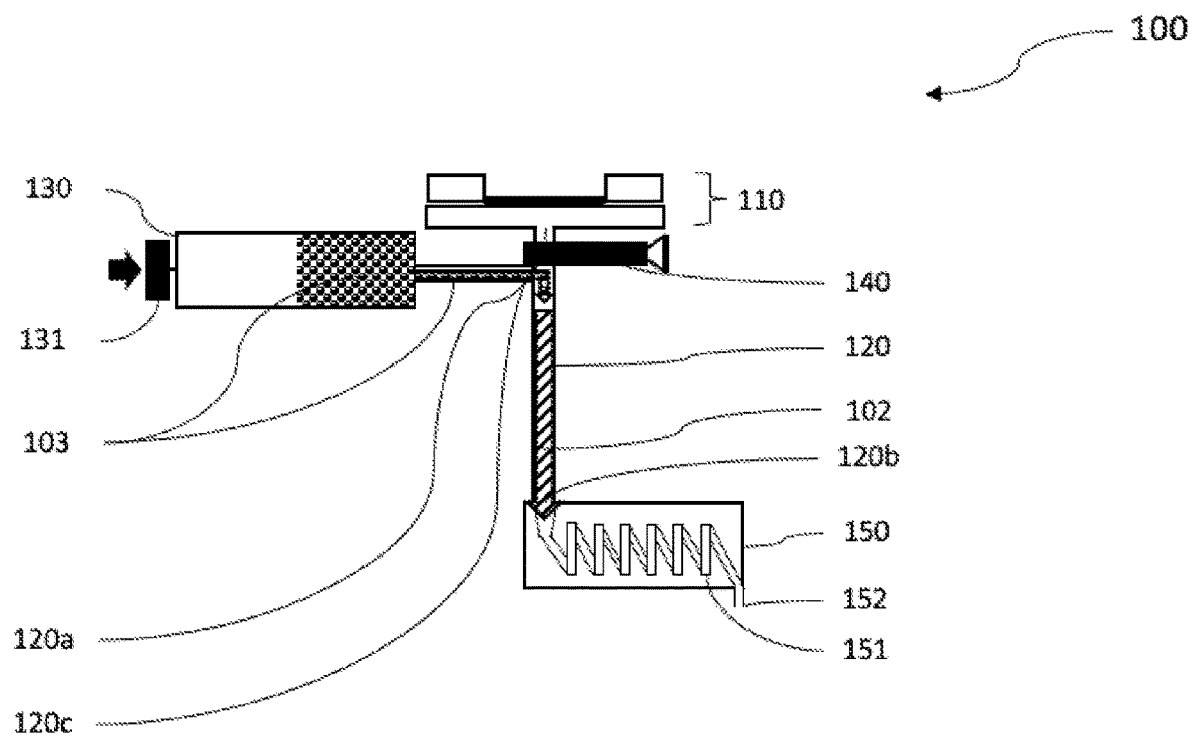

In another preferred embodiment shown in FIG. 5, such a means 140 for preventing any fluidic return can consist of a screw the stroke of which induces a "pinching" of said capillary channel 120. Such a screw can thus be actuated, once the saturation of the capillary channel 120 with blood plasma 102 has been obtained, so as to exert pressure on the capillary channel 120, to pinch and/or close it, thus making it possible to stop any flow of the blood plasma 102 in the direction of the collection module 110. Manual or motorized actuation of such a screw makes it possible for said screw to abut against the capillary channel 120 when it is desired to "close" said channel 120 at the level of its first end 120a.

However, other types of means 140 of preventing any fluidic return to the collection module 110 could consist, for example, of a valve designed for go/no-go applications for which said valve opens or closes as a function of the pressure of the fluid passing therethrough. Valves available on the market known as guillotine or direct-passage valves may be mentioned. Such a valve can furthermore be actuated manually by the user themself, provided that the saturation step 220 has been completed, but it can also be envisaged to automate such an actuation. In the latter case, such a device contains a processing unit, such as a microprocessor, arranged to use the information originating from a sensor designed or positioned to detect the saturation of the capillary channel 120 and produce a closure signal intended for an electrically controlled valve. In a variant, instead of using a sensor, it is possible to imagine the use of a clock, otherwise called a timer. Thus, in such a hypothetical case, the closure signal intended for the electrically controlled valve could be issued on the basis of a predetermined elapsed time.

It should be noted that, due to the fact that such a means 140 for preventing any fluidic return is positioned upstream of the fluidic connection of said storage reservoir 130 with said capillary channel 120 (i.e. substantially at the level of the first end 120a of the capillary channel 120), this also makes it possible to further ensure a constant volume of blood plasma 102 contained in the portion of said capillary channel 120 defined by the length L.

As shown in FIG. 2 and in FIG. 5, a step 230 (in parallel or subsequent to the actuation of the means 140 for prevention of any fluidic return when this requires such an actuation) takes place to induce the forced flow of a reagent 103, contained beforehand in the storage reservoir 130 for a reagent 103, in the capillary channel 120. In this respect, such a storage reservoir 130 can be arranged in the form of a flexible pouch intended to contain a fluid, commonly called a "blister pouch", fluidically connected to the capillary channel 120 by means, for example, of a capillary tube forming a T-junction 120c with the capillary channel 120. Thus, in such an embodiment, the reagent 103 is contained in said flexible pouch and the forced flow of said reagent 103 in said channel 120 can be induced by a mechanical compression carried out by the user of said device 100. In other words, the user themself presses on the flexible pouch in order to release its content (the reagent 103) therefrom into the capillary channel 120. However, a person skilled in the art would not be bound by the shape and/or the design of such a fluid storage reservoir 130. Any other type of storage reservoir, such as for example a syringe that can be actuated by the user, could be used instead of the flexible pouch. In a variant, such storage reservoirs 130 (flexible pouch, syringe or any other type) can contain an actuator 131 arranged to cause a displacement of a piston or a compression thus inducing the forced flow of the reagent 103 into the capillary channel 120. The step 230 would then consist of controlling such an actuator 131 either manually (by the user) or in an automated manner, as with the electrically controlled valve described above in order to prevent any fluidic return to the collection module 110. The processing unit optionally producing a closure signal of said valve would also produce a control signal of such an actuator 131.

Figure 6:
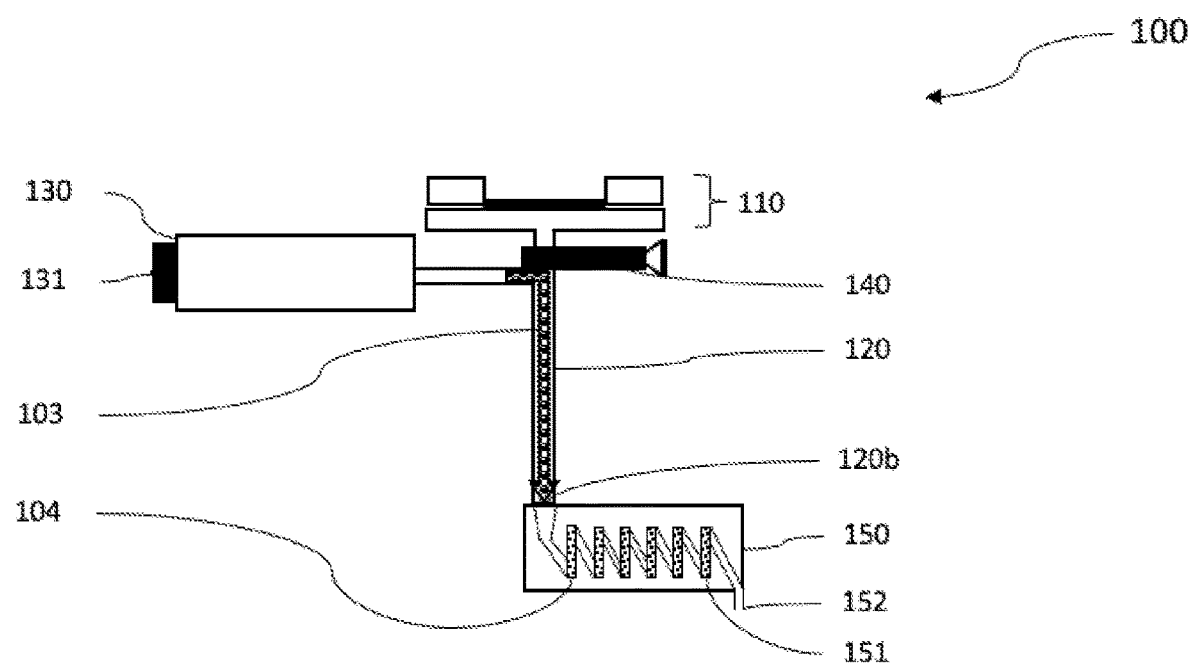

Thus, as shown in FIG. 5 and in FIG. 6, due to the fact of the saturation of the capillary channel 120 with blood plasma 120, the forced flow of the reagent 103 within said channel 120 induces the flow of said blood plasma 102 and of the reagent 103 contained in said capillary channel 120, until reaching said mixing chamber 150 that is in fluidic connection with the second end 120b of said channel 120 (i.e. the lower portion of said channel 120 in the embodiment example shown). In other words, such a forced flow of the reagent 130 acts as a "fluidic piston" in order to set in motion the blood plasma 102 contained in the saturated capillary channel 120, until reaching said mixing chamber 150, within which a homogenous mixture 104 of plasma 102 and of reagent 130 will be obtained. In order to promote and facilitate the passive homogenization of the plasma-reagent mixture 104, said mixing chamber 150 can contain a network of channels 151 arranged for example in zigzags, coils or chevrons. A person skilled in the art would not be bound with respect to the design of the mixing chamber 150 allowing a homogenous fluidic plasma-reagent mixture 104, as any other type of design or structure could be envisaged, such as for example, a structure known as a micropillar structure. Moreover, such a mixing chamber 150 contains an outlet 152 through which said constant homogenous plasma-reagent mixture 104 can flow. Such an outlet 152 thus corresponds to an ejection/evacuation outlet for said plasma-reagent mixture 104 to the outside of said device 100.

Moreover, said microfluidic device 100 for obtaining a plasma-reagent mixture according to the invention is dimensioned so that the volume of said storage reservoir 130 is greater than the sum of the volumes of said capillary channel 120 and of said mixing chamber 150. By way of illustration, but non-limitatively, such a mixing chamber 150 could have a volume of sixty microlitres (capable of corresponding to dimensions of four millimetres in diameter by five millimetres long) to two hundred and fifty microlitres (capable of corresponding to dimensions of five millimetres in diameter by thirteen millimetres long) and the storage reservoir 130 could have a volume of one hundred to three hundred microlitres. Thus, the flow of the blood plasma 102 and of the reagent 103 contained in said capillary channel 120 will occur until said chamber 150 is saturated with plasma-reagent mixture 104, thus allowing the constant flow of a plasma-reagent mixture 104 via the outlet 152 of the mixing chamber 150. A device 100 according to the invention is thus clearly distinguished from the blood transport devices disclosed by the documents US 2014/0309557 and WO 2014/172247A1 by the structures and dimensionings thereof, taking account of the storage and transport function thereof as well as the nature of the fluids intended to flow within them. In fact, the known transport devices are arranged such that the blood sampled and stored, together with a stabilizer or anticoagulant, remain passively within during the transport between the sampling site and the analysis centre. It is only after separation of the plasma by centrifugal force carried out by an item of third-party equipment that a sample of plasma can be extracted from the transport device by means of an actuator provided to facilitate the extraction of the plasma contained via an outlet opening theretofore closed, for analysis purposes. Without the prior action of a centrifuge, said actuator of the known transport devices would only make it possible to extract the blood stored in the blood sample transfer device.

Figure 7:
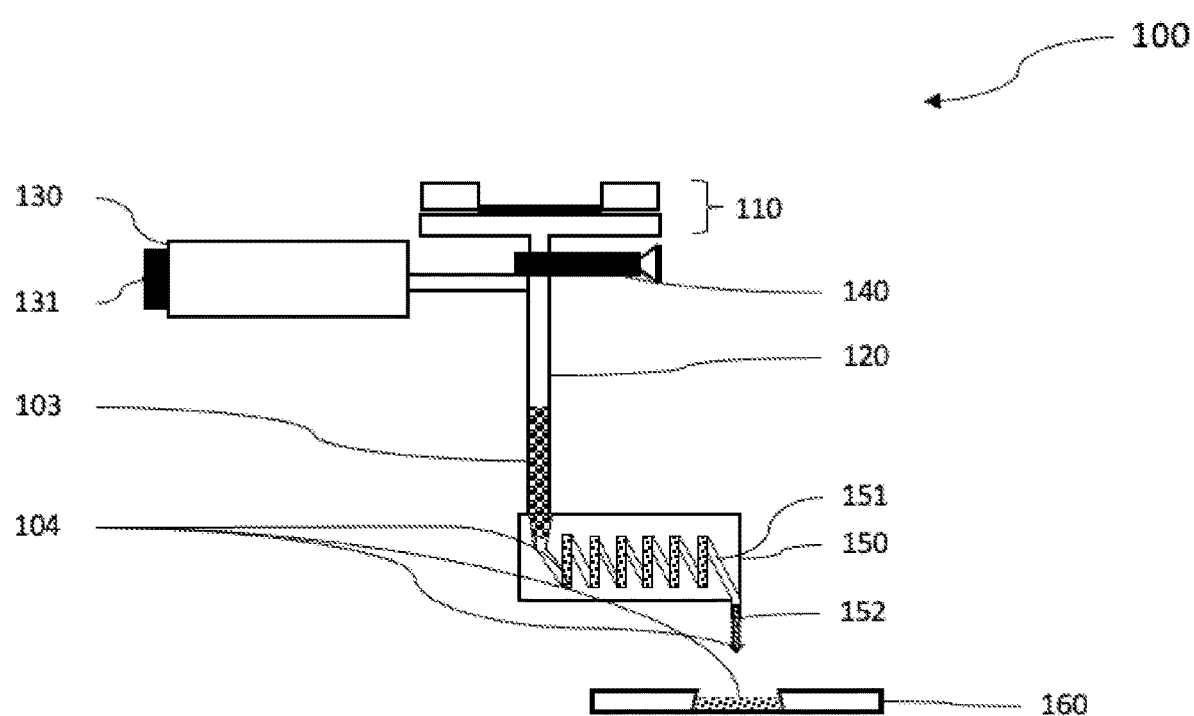

By virtue of the innovative arrangement of a device 100 according to the invention, once the constant homogenous plasma-reagent mixture 104 flows from the outlet 152 of the mixing chamber 150, said method 200 for the implementation of such a microfluidic device 100 for obtaining a homogenous plasma-reagent mixture according to the invention contains a last step 240 of collecting said mixture 104. In a preferred mode of the invention, as shown in FIG. 7, such a step 240 can consist of positioning a reactive strip 160 such as, for example, a lateral flow immunoassay (LFI) strip, downstream of the outlet 152 of said mixing chamber 150. Said mixture 104 can thus be deposited on said reactive strip 160.

Such a reactive strip 160 can be used directly by the user to obtain a quantification of the blood biomarker of interest by positioning said strip 160 in an optical reader, allowing immediate reading/display by the user of the quantified result. Thus, an individual wishing for enhanced health monitoring can take advantage, from their place of residence or on the move, of a system for the quantification of a blood biomarker comprising a microfluidic device 100 for obtaining a homogenous plasma-reagent mixture according to the invention, a reactive strip 160 and an optical reader. Such a system could contain means for wired or wireless communication with a remote computer entity in order to transmit quantification results. Such a computer entity can consist of a mobile electronic object (portable computer, touchscreen tablet or smartphone) hosting a software application or appropriate computer program making it possible for example to record results and/or constitute a medical dashboard or a history of the analyses carried out.

A person skilled in the art would understand that the present disclosure is not limited to that which is specifically shown and described above. Other modifications can be envisaged without departing from the scope of the present invention defined by the claims attached hereto. In particular, in the preferred example described above, the device 100 contains one capillary channel. However, in order to increase the capillarity force exerted on the plasma present in the collection module 110, a device 100 can contain several capillary channels (two, three or even more) opening on the one hand into the collection module 110 and on the other hand, into the mixing chamber 150, optionally via a "parent" collection channel. Furthermore, mention has been made in the present application of a capillary channel favouring industrial use as being non-deformable. However, in a variant, a capillary tube could be used.

The invention claimed is:

1. A microfluidic device for obtaining a homogenous plasma-reagent mixture comprising:
a collection module for blood;
a first capillary channel having a first end in fluidic connection with said collection module;
a storage reservoir for a fluid in fluidic connection with said first capillary channel;
a mixing chamber in fluidic connection with a second end of the first capillary channel arranged to passively induce a homogenous mixture of fluids originating from said first capillary and having a flow outlet of said homogenous mixture;
a means for preventing any fluidic return to the collection module wherein:
the collection module comprises:
a semi-permeable membrane arranged to receive a quantity of blood and designed to separate the blood constituents, by gravity when said semi-permeable membrane is substantially horizontal, according to the sizes thereof and thus to trap said constituents other than the blood plasma;
a specific surface arranged between said semi-permeable membrane and the first end of the first capillary channel and having hydrophobic, hydrophilic and surface tension properties in order to extract the blood plasma from the semi-permeable membrane and cause said blood plasma to flow in said first capillary channel;
the first capillary channel has determined dimensions (L) between the fluidic connection of said storage reservoir (130) with the first capillary channel and said second end of said first capillary channel, in order to control the quantity of blood plasma when the first capillary channel is saturated with blood plasma;
the fluid contained in the storage reservoir is a reagent intended to be mixed with the blood plasma;
said storage reservoir is arranged to:
contain a volume of reagent greater than the sum of the fluid volumes that the first capillary channel and the mixing chamber can contain;
have an actuator designed to induce a forced flow of said reagent in the first capillary channel driving a flow of a homogenous plasma-reagent mixture through said flow outlet of the mixing chamber when said actuator is controlled after saturation of the first capillary channel with blood plasma.

2. The microfluidic device for obtaining a homogenous plasma-reagent mixture according to claim 1, for which the first end of the first capillary channel is positioned substantially at the centre of said plasma collection module.

3. The microfluidic device for obtaining a homogenous plasma-reagent mixture according to claim 1, for which the collection module contains a membrane holder arranged in order to concentrate the blood on said semi-permeable membrane.

4. The microfluidic device for obtaining a homogenous plasma-reagent mixture according to claim 1, for which the specific surface is constituted by polymethyl methacrylate, a thermoplastic polymer, polyacrylamide, polyurethane, poly (hydroxyethyl acrylamide) or polyethylene glycol derivatives.

5. The microfluidic device for obtaining a homogenous plasma-reagent mixture according to claim 1, for which said mixing chamber contains a network of channels respectively arranged in zigzags, coils or chevrons, to passively induce said homogenous plasma-reagent mixture.

6. A method for implementation of the microfluidic device for obtaining a homogenous plasma-reagent mixture arranged according to claim 1, said method containing:
a step of depositing blood or blood plasma on the semi-permeable membrane of the plasma collection module, when said device is positioned such that the semi-permeable membrane is horizontal;
a step of saturating the first capillary channel with blood plasma;
a step, after said step of saturating the first capillary channel with blood plasma, of controlling the actuator of the storage reservoir inducing the forced flow of a reagent, contained beforehand in said storage reservoir, into the first capillary channel following saturation of the mixing chamber;

a step of collecting a homogenous plasma-reagent mixture from the flow outlet of the mixing chamber.

7. The method for implementation of the microfluidic device of a microfluidic device for obtaining a homogenous plasma-reagent mixture according to claim 6, for which the step of saturation of the first capillary channel with blood plasma consists of waiting, as soon as the blood plasma flows in the first capillary channel, for a predetermined duration, as a function of the dimensioning of the first capillary channel.

8. The method for implementation of the microfluidic device of a microfluidic device for obtaining a homogenous plasma-reagent mixture according to claim 6, for which the step of collecting the homogenous plasma-reagent mixture (104) consists of positioning a reactive strip downstream of the outlet of the mixing chamber such that said strip collects all or part of said homogenous plasma-reagent mixture.

\* \* \* \* \*